United States Patent [19]

Downing, Jr.

[11] 4,333,476

[45] Jun. 8, 1982

[54] COMPREHENSIVE PULMONARY MEASUREMENT TECHNIQUE

[76] Inventor: Willis G. Downing, Jr., 9430 Tujunga Canyon Blvd., Tujunga, Calif. 91042

[21] Appl. No.: 969,962

[22] Filed: Dec. 15, 1978

[51] Int. Cl.$^3$ .............................................. A61B 5/08
[52] U.S. Cl. ................................... 128/720; 128/728
[58] Field of Search ....................... 128/716, 718–720, 128/724, 725, 727, 728, 730

[56] References Cited

U.S. PATENT DOCUMENTS

| 3,410,264 | 11/1968 | Frederik | 128/720 |
| 3,527,205 | 9/1970 | Jones | 128/728 X |
| 3,598,111 | 8/1971 | Kahn et al. | 128/720 |
| 3,713,436 | 1/1973 | Hardway, Jr. | 128/720 |
| 3,726,270 | 4/1973 | Griffis | 128/719 |
| 4,036,222 | 7/1977 | Gillard et al. | 128/720 |
| 4,051,843 | 10/1977 | Franetzki et al. | 128/720 |
| 4,122,839 | 10/1978 | Franetzki et al. | 128/720 |

OTHER PUBLICATIONS

Goldman et al., "A Simplified Measurement of Resp. Resist." J. App. Phys., vol. 28, No. 1, Jan. 1970.
Ross et al., "Direct Readout . . . Impedance", Med. & Biol. Eng., vol. 14, No. 5, pp. 558–564, Sep. 1976.
Finucane et al., "Estimation of Alyeoler Pressure . . . ", J. App. Phys., vol. 38, No. 3, pp. 531–537, Mar. 1975.
Murphy et al., "A Dynamic Compliance Computer . . . ", J. App. Phys., vol. 36, No. 5, pp. 629–633, May 1974.
Comroe, Jr. et al., "Design of Butyl Plethys. . . . , J. App. Phys., vol. 14, May 1959, pp. 439–444.

Primary Examiner—Lee S. Cohen
Attorney, Agent, or Firm—Poms, Smith, Lande & Rose

[57] ABSTRACT

The resistance of the lung is measured by the present technique both for unidirectional air flow and for alternating direction air flow at various points as a person rapidly exhales a maximum breath of air, and these measurements, together with other lung characteristic measurements provide comprehensive data for lung diagnosis and analysis. The equipment which is used is a closed system, and includes an input spirometer from which the subject draws air, and an output plastic air bag into which exhaled air is exhausted. A loudspeaker operated at 10 to 12 cycles per second supplies alternating air pressure signals to the mouth through a substantially conical or tapered transition to provide a good impedance match. Signals are recorded from an esophageal balloon system which measures lung pressure from inhalation and exhalation air rate sensors, and from a transducer which measures the pressure at the mouth. Suitable compensation and coupling networks are employed to compensate for the frequency response of the transducer systems, such as the esophageal balloon sensor. The input gas from the spirometer is free of nitrogen, and a mass spectrometer is employed to detect nitrogen exhaled by the subject to determine residual levels of air in the lungs.

17 Claims, 13 Drawing Figures

(a) SLOW EXHALATION

Fig. 12

(b) FAST EXHALATION (MAXIMAL)

RV = 1.6ℓ; TLC = 6.5ℓ

COMPREHENSIVE PULMONARY MEASUREMENT TECHNIQUE

FIELD OF THE INVENTION

This invention relates to pulmonary and respiratory measurement techniques and apparatus.

BACKGROUND OF THE INVENTION

Various apparatus have been proposed heretofore for measuring the resistance of the lungs and other physiological characteristics of the lungs, both on an alternating pressure and on a unidirectional pressure basis. However, most of these prior proposed arrangements have been open systems, or have been directed to the analysis of a single or only a few pulmonary characteristics. Accordingly, the results obtained from such prior tests tend to be incomplete and relatively inconclusive, although many of the prior art arrangements were quite useful in obtaining preliminary insights into certain pulmonary functions and phenomena.

Accordingly, a principal object of the present invention is to provide a more complete and comprehensive technique for the analysis of pulmonary functions and effects, both under unidirectional and alternating pressure conditions, and to combine this information with a complete analysis of the volumes of air inhaled and exhaled by the subject, particularly under maximum expiratory air flow conditions.

SUMMARY OF THE INVENTION

In accordance with one important feature of the invention, the resistance of the lungs, both to unidirectional air flow and to alternating pressure air flow, is compared at different levels of exhalation, and the coincidence and divergence of the steady and alternating flow resistance characteristics are employed in analysis and diagnosis, both of the individual patient and also of the three principal effects which have been hypothesized to account for maximal expiratory flow limitations.

In accordance with another aspect of the invention, the equipment which is employed includes both arrangements for measuring inhaled air, and also for measuring exhaled air; and a fully impedance matched source of alternating pressure coupled to the mouthpiece by which the system is used by the subject under examination.

Other features of the invention include (1) the use of a closed system, (2) the use of an esophageal balloon to measure the pressure across the lungs, (3) the use of a fully compensating network to couple signals from components, such as the esophageal balloon transducers to the recording apparatus without adverse effects from the frequency characteristic of the esophageal balloon system), and (4) the use of a mass spectometer to analyze the exhaled gases.

An important feature of the present invention is the fact that the apparatus may be employed to perform, in addition to the special test mentioned above, most of the standard pulmonary function tests, including (1) maximal expiratory flow measurements, (2) closing volume tests, (3) nitrogen washout tests, (4) residual volume determination, (5) total lung capacity, (6) lung impedance (resistance, compliance and inertance) to both steady and sinusoidal flow. Under normal testing conditions, separate instruments would be required for these measurements.

Other objects, features, and advantages of the present invention will become apparent from a consideration of the following detailed description and from the accompanying drawings.

DETAILED DESCRIPTION

In the field of dynamic pulmonary and respiratory analysis and diagnosis, it has long been known that there is a fixed upper limit to maximal expiratory gas flow velocity. On a historical basis, there have been three mechanisms which have been postulated as causes of expiratory flow impedance. These three mechanisms or effects are known as (1) airway closure, (2) selective merging, and (3) flow limitation at Mach I or at wave velocity.

Figure 1:
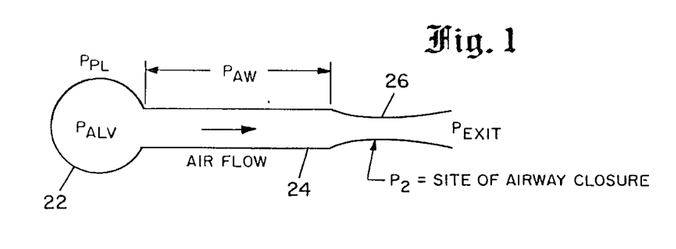
FIG. 1 is a diagram representing the effect known as "airway closure" which may limit maximum expiratory air flow from the lungs.

FIG. 1 is a diagram representing the phenomenon of airway closure. In FIG. 1, an alveolus 22 is connected to a bronchial tube 24 and a zone 26 is indicated where the bronchial tube might close partially or wholly. The theory of the mechanism of airway closure is that, as the exhaled flow level increases, the resistive pressure drop from alveoli to points in the air ducts downstream, increases to such an extent that at these points, such as point 26 in FIG. 1, the pressure inside the airways is equal to or less than the lung pressure bearing inward from outside of the airways. It is at this moment that airway closure supposedly begins. As the outside lung pressure increases, so does airway closure, thus increasing flow impedance. Although there are other objections to airway closure as the cause of a maximal flow limit, the most obvious, logical flaw is the following: the limit of airway closure is airway collapse. Complete airway collapse results in zero air flow, which is not consistent with a high flow rate maximum observed at the start of flow limitation during the maximum expiratory flow test.

Figure 2:
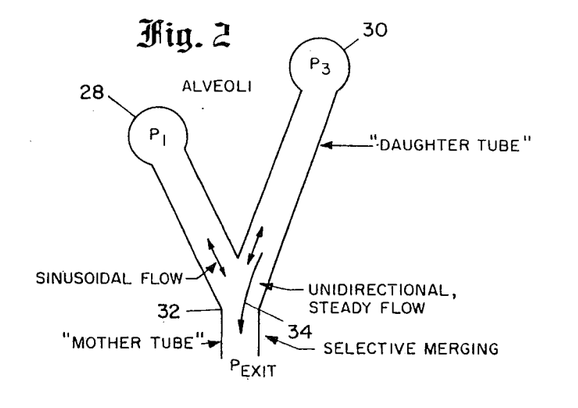
FIG. 2 is a similar diagram representing the effect known as "selective merging" which may limit expiratory flow rates.

The second mechanism, known as "selective merging" is diagrammed in FIG. 2. This mechanism depends on an increase in the lateral pressure gradient from the rib cage to the center of the lungs as positive pressure applied to the lungs by the rib cage and diaphragm increases. As the pressure gradient increases, the difference in pressures between individual alveoli such as that shown at 28 and 30 in FIG. 2, also increases. Thus, at an airway junction, such as junction 32 in FIG. 2, the pressure from one bifurcating tube may exceed that from the other. The result is that flow from the duct having higher pressure takes over and blocks the gas flow from the joining duct. It may even go upward into the second "daughter tube". As the pressure gradient increases, the number of airway junctions at which selective merging occurs increases. The effect of the increasing extent of selective merging is to decrease the total volume of lung air passageways participating in unidirectional "steady" expiratory flow, and this is indicated by the arrow 34 which extends only from the alveolus 30, as there is no unidirectional or steady flow from the alveolus 28. On the other hand, sinusoidal flow, as represented by the double-headed arrows, takes place at junction 32 to both of the passageways associated with alveoli 28 and 30.

Figure 3:
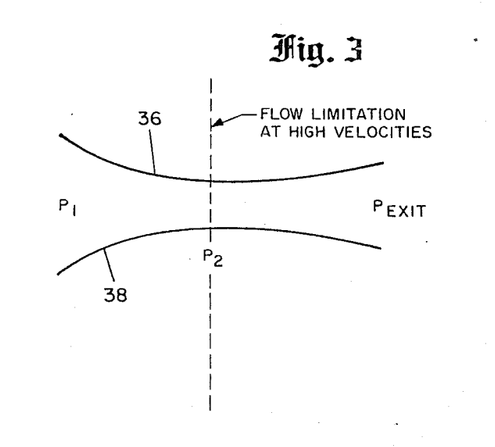
FIG. 3 represents the effect known as "flow limitation at Mach I, or at wave velocity" which may limit flow of air from the lungs.

The third primary mechanism of flow limitation which has been hypothesized is "flow limitation at Mach I, or at wave velocity". While this was originally referred to principally as "flow limitation at Mach I", it now appears probable that the actual speed of sound in open space would not be reached. However, the wave velocity within a bronchial passageway may be much less than the velocity of sound in free space, and it appears possible that some such limitation may contribute to maximal expiratory flow limits. The simple diagram of FIG. 3 shows a constriction 36 in the overall air passageway 38. Specifically, the constriction 36 where the highest flow rate will occur, may well be at the throat.

Figure 4:
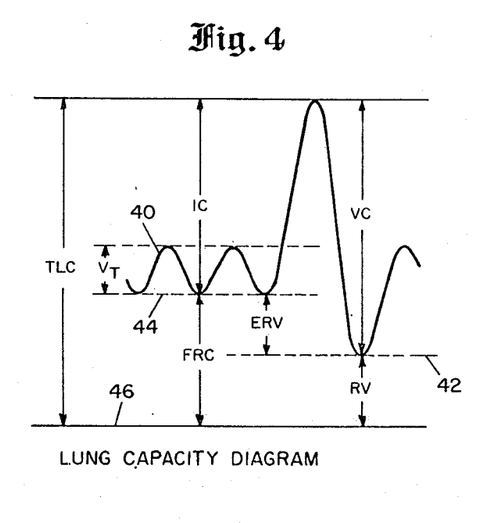
FIG. 4 is a diagram which is useful in considering lung capacity and diagnosis.

Now, referring to FIG. 4, this diagram represents the lung capacity, and the arrow designated "TLC" indicates the total lung capacity. Normal breathing is represented by the sinusoidal curve 40 having a total amplitude $V_t$ known as the tidal volume. When a subject is requested to take a very deep maximal breath, this is represented by the arrow designated "IC", which stands for inspiratory capacity. On a maximal exhalation, which is frequently employed in the diagnosis of lung diseases or the like, the volume which is expelled is indicated by the arrow designated "VC", referring to the "vital capacity". It may be noted that even after a full exhalation, the lungs still have a residual volume, which is designated "RV". In the tests which will be discussed below, the subject is normally requested to make as complete an exhalation as possible, and then draw in air from a controlled source which could be pure oxygen or oxygen combined with another gas other than nitrogen, so that the residual volume (which would of course include nitrogen) could be measured in the course of subsequent tests for nitrogen in the exhalations. Referring once more to FIG. 4, the letters "ERV" stand for expiratory reserve volume, which essentially is the difference between the volume following a normal rest exhalation and a maximal exhalation which would bring the lung volume down to the dashed line designated 42 in FIG. 4. It may also be noted that the letters "FRC" stand for the functional residual capacity, which is the difference between the volume indicated by line 44 after a normal exhalation and the entire residual of capacity or volume in the lungs where the line 46 represents zero.

Figure 5:
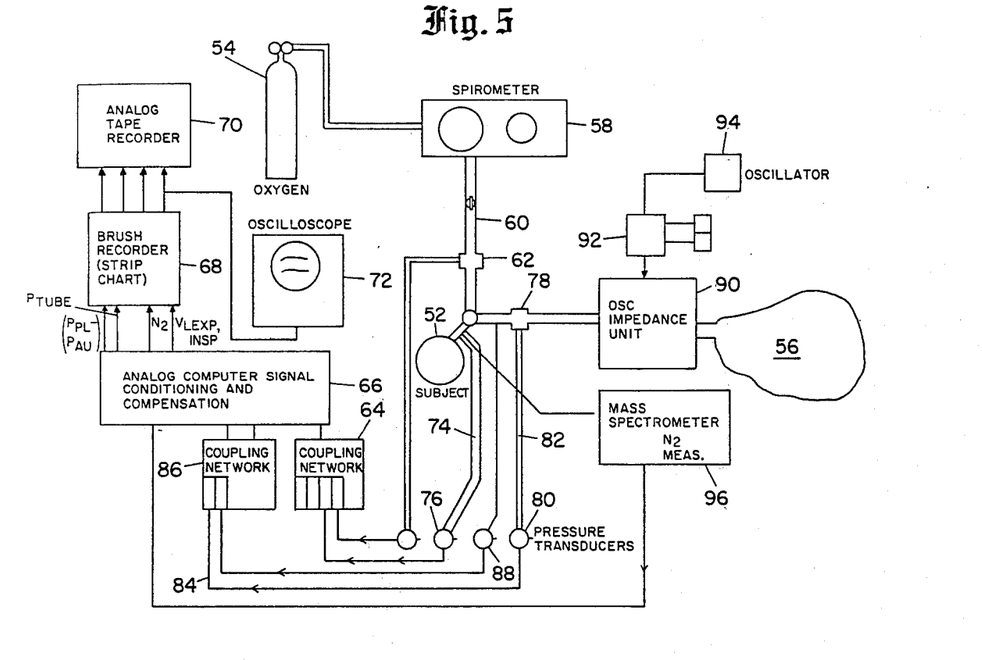
FIG. 5 is a diagram of the apparatus employed in the lung tests of the present invention.

Referring now to FIG. 5, it shows the subject 52, an input tank of pure oxygen 54, and an output plastic bag 56 where the exhalations from the subject are eventually collected. Oxygen from the tank 54 is supplied to the subject 52 through the spirometer 58 which accurately measures the gas, which is supplied to the channel 60 and eventually to the mouthpiece by which the subject inhales the oxygen. A sensor 62 for determining the flow rate of inhaled air may be implemented by a screen-type pneumotachograph. The output signals from the sensor 62 are supplied to the coupling network 64, to the analog computer signal conditioning and compensation circuitry 66, and to the strip chart recorder 68 and the analog tape recorder 70, as well as to the oscilloscope 72. The esophagael balloon inputs 74 and transducer 76 are indicated schematically in FIG. 5, and they are coupled to the network 64 and the analog computer circuit 66.

The flow rate of the exhaled air is also measured by the sensor 78, which may, for example, be a Fleisch pneumotachograph, made by Instrumentation Associates, Inc. The pressure transducer 80 which receives inputs 82 from the pneumotachograph 78, provides an output signal on lead 84 to the coupling network 86. Similarly, the transducer 88 which provides pressure output signals is connected to coupling network 86, which in turn supplies output signals to the analog computer signal conditioning and compensating circuit 66 mentioned hereinabove. Alternating pressure signals are provided by the impedance unit 90, which is essentially a "woofer" type speaker, which is driven by the power amplifier 92 under the control of oscillator 94. Most of the tests which were conducted operated the speaker 90 at a frequency of 10 or 12 cycles per second, and it is preferably operated at a frequency above 6 cycles per second. It is to be understood, of course, that other frequencies of operation could be employed, and also that different wave forms could be utilized. More specifically, for example, square waves, or even random noise patterns could be supplied by the loudspeaker unit 90.

The mass spectrometer 96 is coupled to the output from the subject's mouth, and may be employed to determine the level of nitrogen present in the exhalations, throughout the exhalation. As mentioned above, in practice, the subject is requested to initially exhale fully into the atmosphere, and then to inhale through the mouthpiece from the spirometer 58, with the maximal intake breath being free of nitrogen. Thus, if the subject exhales to the volume indicated by line 42 in FIG. 4, then the residual volume RV will still contain some nitrogen, and the intake breath having a volume VC will dilute the nitrogen, and subsequent exhalations will indicate the portion of nitrogen present. Of course, after several inhalations from the nitrogen-free gas supply from spirometer 58, very little nitrogen will be present in the exhalations. However, the amount of nitrogen present in the initial exhalations will permit a calculation of the residual volume RV of the subject, and other parameters useful in diagnosing the pulmonary functions of the subject.

Figure 6:
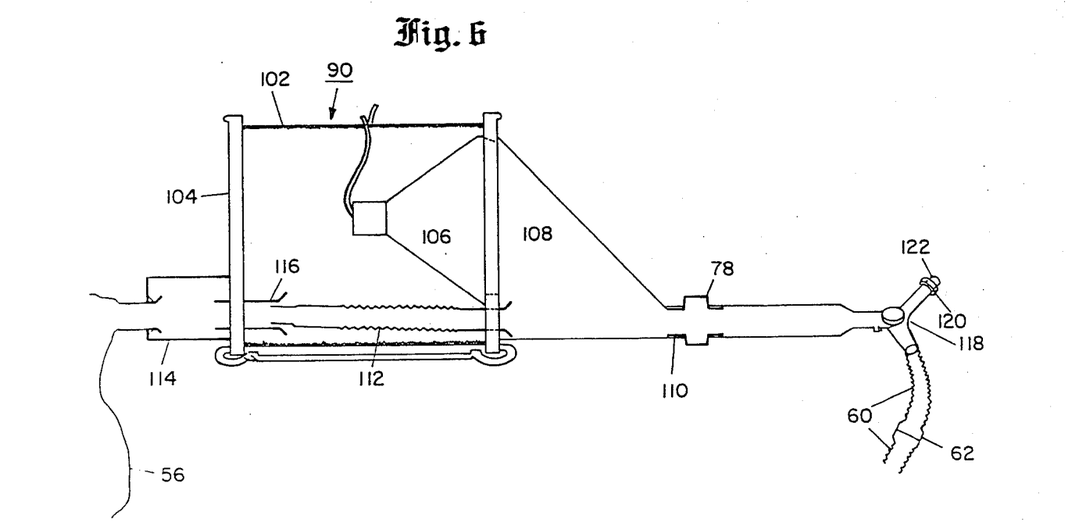
FIG. 6 is a diagram showing the impedance matching arrangements between the source of alternating pressure and the mouthpiece.

FIG. 6 shows the mechanical construction of some of the components shown schematically in FIG. 5, in greater detail. More specifically, the oscillatory impedance unit 90 includes the outer cylindrical wall 102, the end cap 104, and the woofer-type loud speaker unit 106 connected to an off-set funnel impedance matching structure 108. More specifically, with regard to the shape of the impedance-matching structure 108, it is of a diameter substantially equal to the cylindrical diameter of the unit 90 at its left-hand end as shown in FIG. 6, and has a circular configuration to fit the channel 110, at its right-hand end, and is substantially uniformly tapered in both the horizontal and vertical plane to provide a uniform transition from the larger cross-section to the smaller cross-section.

Concerning other parts of the system as shown in FIG. 6, they include the duct 112 and the plastic bag 56 which ultimately receives the exhaled air. The connecting member 114 secured to the end cap 104, and the tube 116 are also shown. The tube 116 is a flow shaping low inertance and resistance exit from the drum unit. Note that the tube 112 points into the structure 116, but that they are not directly connected, to avoid undue resistance to oscillation for the cone of the speaker 106.

At the right in FIG. 6 may be seen the flow measuring structure 78 in the tube 110, and the flow measuring pneumotachograph 62 in the tube 60 from the spirometer to the junction 118. Incidentally, the Y junction 118 is a low turbulence three-way Y valve to permit the subject to inhale air from the spirometer over tube 60, and to then direct exhalations through channel 110. The mouthpiece 120 is provided with a cork 122 to seal the space within the system when not in use.

As mentioned above, the pressure transducers shown in FIG. 5 have two inputs, and as a result of the difference in pressure between the two tubes which connect to each of the pressure transducers, an output electrical signal is produced. In the case of some of the transducers, such as unit 88, there is only one input tube shown connected to the transducer, and the pressure on the other side of the transducer is atmospheric pressure, and accordingly, the output from transducer 88 is the difference between the pressure at the mouth of the subject and atmospheric pressure.

It was also mentioned that transducer 76 receives its pressure input from an esophageal balloon, and for completeness, it is noted that one typical prior art reference to such an arrangement is included in an article entitled, "The Measurement of Intraesophageal Pressure and its Relationship to Intrathoracic Pressure", by Donald L. Fry, et al, Journal of Laboratory Clinical Medicine, Volume 40, pages 664 et seq., 1952.

Figure 7:
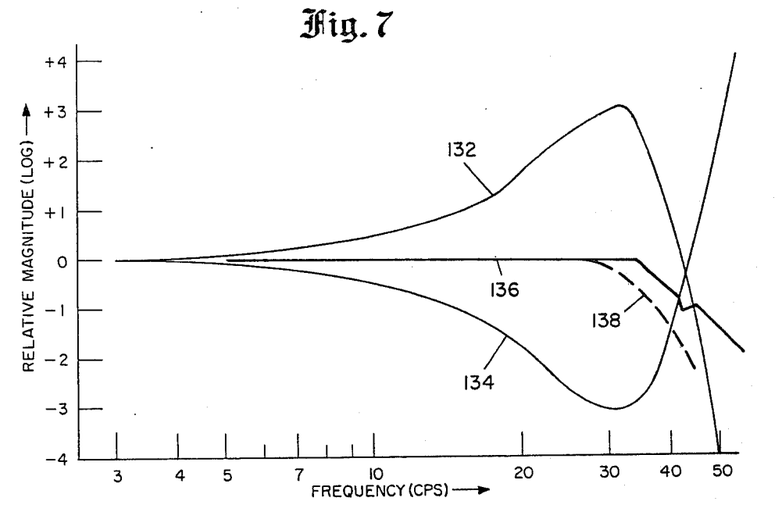
FIG. 7 is a plot of relative amplitude versus frequency for the esophageal balloon transducer system and the compensating network.

Now, referring to FIG. 7, the plot 132 shows the response characteristic of an esophageal balloon and transducer arrangement employed in the present experiments, and which were similar to those disclosed in the Fry article. The plot 132 of FIG. 7 is a plot of relative magnitude on a logarithmic scale against frequency. Within the circuit designated 66 in the schematic diagram of FIG. 5 is a compensating network to compensate for the response characteristic 132 as shown in FIG. 7 (and also for its phase shift as disclosed below). More specifically, the compensation network included in the circuit block 66 of FIG. 5 has a characteristic as shown at 134 in FIG. 7. The resultant corrected characteristic is that which appears at 136 in FIG. 7. In addition, to avoid the possibility of undesired high amplitude and possible oscillation at higher frequencies, a third order Butterworth filter network having a response characteristic approximately as indicated by the dashed line 138 in FIG. 7 is included in the compensation network.

Figure 8:
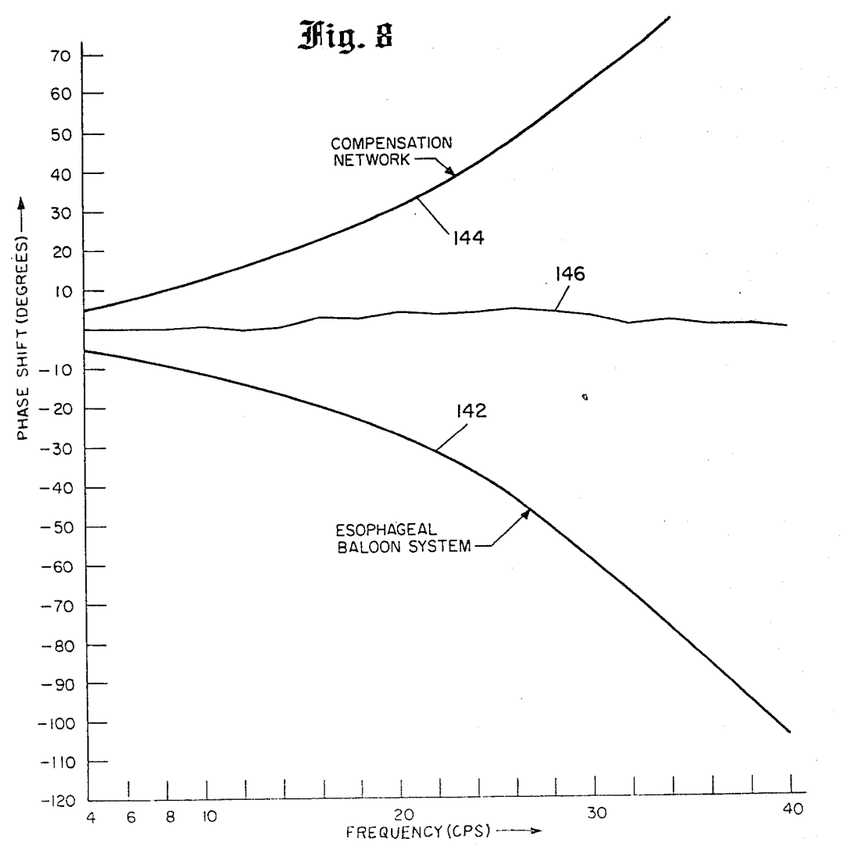
FIG. 8 shows the phase shift versus frequency characteristic of the esophageal bag system and its associated compensation network.

FIG. 8 is a phase shift compensation diagram, showing the phase shift characteristic 142 of the esophageal balloon system, the phase shift characteristic 144 of the compensation network, and the resulting corrected characteristic 146, which includes both the esophageal balloon system and the compensation network.

Figure 9:
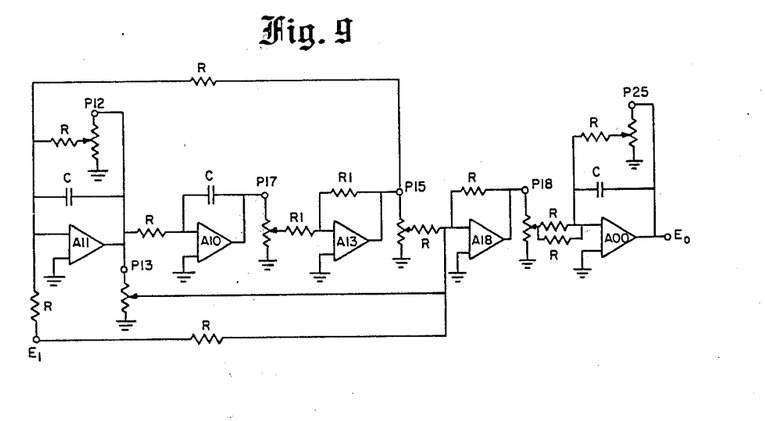
FIG. 9 is a circuit diagram of the compensation network which is plotted in FIGS. 7 and 8.

The circuit of FIG. 9 represents the compensation network, including both the compensation characteristics and the third order Butterworth filter as mentioned above in connection with FIG. 7. In the following Table I, the parameters for the compensation circuit of FIG. 9 are set forth in detail. In Table I, the formula which is set forth gives the guiding parameters for the compensation circuit of FIG. 9. Further, it may be noted that the terms in the numerator primarily represent the straight compensation characteristic, as represented for example by curve 134 in FIG. 7, while the third order Butterworth filter, as indicated by the dashed line curve 138 in FIG. 7 is implemented by the denominator terms in the equation.

TABLE I

PARAMETERS FOR COMPENSATION CIRCUIT OF FIG. 9

A = inverting amplifier
C = capacitor = .02 microfarads
P = potentiometer
R = resistor = 100K ohms
R1 = resistor = 10K ohms $$\frac{E_o(s)}{E_i(s)} = \frac{s^2 + 173.88s + 4.9 \times 10^4}{s^2 + 298.8s + 8.92 \times 10^4} \cdot \frac{1}{s + 298.8}$$

$s = j\omega$

Pot Settings:
P12,P25 = .6047
P13 = .2518
P15 = .5013
P17 = .3996
P18 = .5573

Figure 10:
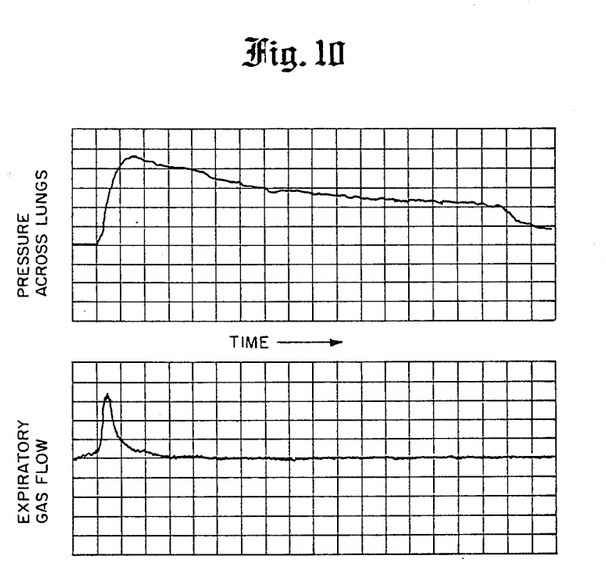
FIG. 10 includes two plots, one of the pressure across the lungs and the second being the expiratory gas flow for a maximum exhalation.

FIG. 10 shows the pressure across the lungs in the course of a maximum expiration by the subject, corresponding to an expiration of the volume indicated by the arrow VC in FIG. 4, for example. In looking closely at the characteristic in the upper plot of FIG. 10, it may be seen that, superimposed on the basic pressure characteristic, is an alternating current pattern which represents the alternating pressure produced by the speaker 106, shown in FIG. 6. In the lower plot of FIG. 10, the expiratory gas flow is shown. In comparing these two plots which relate to a single maximum expiration from a single subject, it is interesting to see that the bulk of the gas is expelled during the initial portion of the cycle, and despite a relatively high pressure across the lungs during the remainder of this cycle, the gas flow is greatly reduced.

Figure 11:
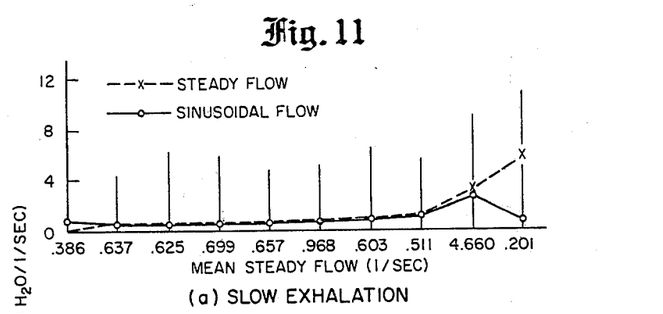
FIGS. 11 and 12 show steady and sinusoidal flow for a slow exhalation and for a maximal fast exhalation, respectively.
Figure 12:
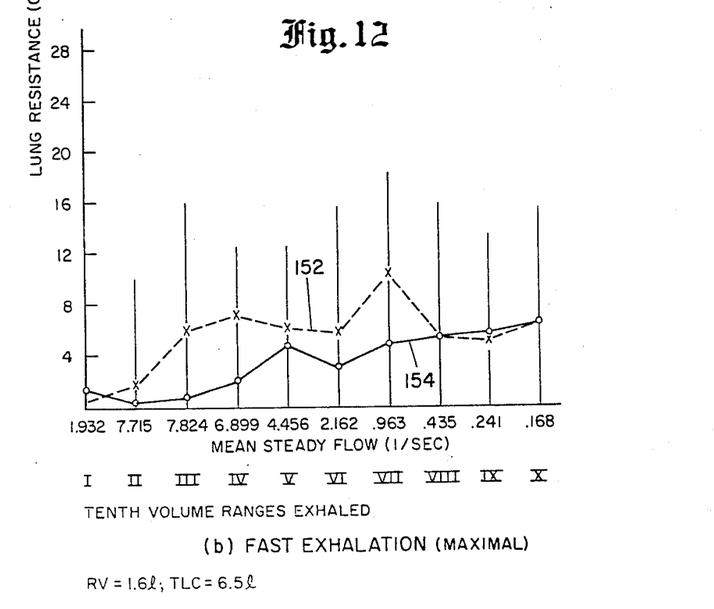

The plots of FIGS. 11 and 12 show lung resistance plotted against the volume of air which has been exhaled, for a slow steady exhalation in FIG. 11, and for a maximal exhalation as shown in FIG. 12. In both FIG. 11 and FIG. 12, the dashed line plot represents the resistance to steady flow, and the solid line plot represents resistance to sinusoidal or alternating pressure flow.

In examining these interesting results, the first matter to be noted is the fact that the resistance for steady air flow, and for alternating air flow during a slow exhalation was approximately the same. For a fast or maximal exhalation, however, as shown in FIG. 12, there was a significant divergence for the steady flow as shown by the dashed line characteristic 152, as compared with the alternating pressure flow, as shown by the solid line plot 154 in FIG. 12. Incidentally, referring back to the three effects shown diagrammatically in FIGS. 1, 2, and 3, the concurrent changes in resistance would indicate that the effects of airway closure and of flow limitation at high velocities might be present; and departures from concurrent changes in the two plots would indicate that the effect referred to as "selective merging", and illustrated in FIG. 2, may be making a significant contribution to the maximal flow limitation.

The form of the plots of FIGS. 11 and 12 deserve special attention, and it is again noted that they involve on the horizontal scale successive tenths of the total volume which is exhaled in the course of a maximal exhalation. Thus, where most of the volume of air is exhaled during the first portion of the cycle, the horizontal axis would not conform to time with any degree of accuracy; instead, the first six or seven sections of the plot would be compressed to an extreme degree, if a time plot were to be substituted for the volume fractions employed in these plots.

Figure 13:
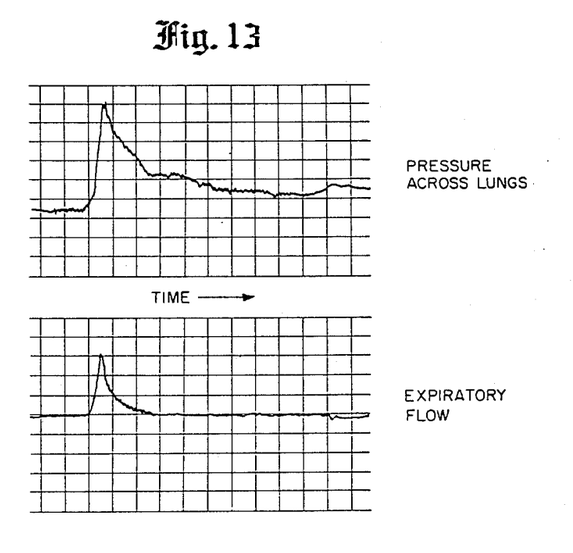
FIG. 13 shows a plot of the pressure across the lungs and the expiratory flow for a different subject than that plotted in FIG. 10.

In FIG. 13, the pressure versus time and the expiratory flow rate versus time are shown for a different subject. In the plot of FIG. 13, the alternating pressure may be seen somewhat more clearly than in the upper plot of FIG. 10. In addition, the plot of FIG. 13 is usefully included to show the considerable differences between subjects which may be tested.

In closing, and for completeness, reference is made to a prior article in which a loudspeaker is employed in a lung measurement apparatus. This article is entitled, "A Simplified Measurement of Respiratory Resistance by Forced Oscillation", by Michael Goldman et al., Journal of Applied Physiology, Volume 28, No. 1, January 1970, pages 113 through 116. In the tests described in this prior article, an open system was employed, and a speaker with no impedance matching arrangements was operated at about three cycles per second during normal breathing of the subject. As mentioned above, the described apparatus was severely limited, and the completeness of the tests which could be undertaken in view of the open nature of the system. Further, no impedance matching, or compensation circuitry of this type described herein was undertaken, nor was any examination made of maximal exhalations or of the variable resistance during different portions of the exhalation cycle.

It is also noted that the present invention is not limited to the precise structure and circuitry disclosed in the foregoing detailed description and in the drawings. By way of example, and not of limitation, a different form of esophageal balloon with a somewhat different frequency characteristic could be employed, and a corresponding compensation network utilized. Similarly, other types of flow meters and measuring equipment may be utilized. Also, alternative apparatus may be utilized for supplying input gas and for recording the output signals from the various transducers. In addition, as well as resistance measurements, other impedance components including separate measurements of compliance and inertance (corresponding to capacitive and inductive impedance, respectively) are readily determined using the present apparatus, and techniques. Accordingly, the present invention is not limited to the precise construction disclosed hereinabove.

What is claimed is:

1. An apparatus for the comprehensive measurement of pulmonary functions comprising:

a source of gas which includes no nitrogen;

a closed pulmonary measurement system including an input spirometer coupled to said source of gas for supplying a measured quantity of said gas excluding nitrogen from said source to a subject;

means for collecting gas exhaled by the subject;

means for supplying alternating pressure signals to the mouth of a subject;

means for measuring the flow of air exhaled by the subject;

means for continuously measuring the nitrogen content of the exhaled air;

means for determining the resistance of the lungs to both steady state and alternating air flow during various portions of a breathing cycle; and means for recording and correlating all of said measured and determined values.

2. An apparatus as defined in claim 1, further comprising:

an esophageal balloon and transducer system having a predetermined frequency response for supplying signals to said apparatus representing the pressure across the lungs;

compensation circuit means connected to receive said signals representing the pressure across said lungs, and for correcting the frequency variations of said signals within the frequency range of interest and extending above the normal frequency of operation of said means for supplying alternating pressure; and means for supplying signals derived from said circuit means to said recording and correlating means concurrently with the recording of the other measured and determined values.

3. An apparatus as defined in claim 1, wherein said means for supplying alternating pressure signals includes a low frequency speaker, and tapered air channel impedance matching means for coupling said speaker to the mouth of the subject; and further comprising direct duct means bypassing said speaker for receiving forceful exhalations from said subject while the subject is receiving alternating pressure signals and directing the air included in such exhalations to the collecting means.

4. An apparatus for the comprehensive measurement of pulmonary functions comprising:

means for supplying alternating pressure signals to the mouth of a subject;

means for measuring the flow of air exhaled by the subject;

means for determining the resistance of the lungs to both steady state and alternating air flow during various portions of a breathing cycle;

an esophageal balloon and transducer system having a predetermined frequency response for supplying signals representing the pressure across the lungs;

compensation circuit means connected to receive said signals representing the pressure across said lungs, and for correcting the frequency variations of said signals within the frequency range of interest and extending above the normal frequency of operation of said means for supplying alternating pressure; and means for recording information representing the measured air flow and the corrected signals from said compensation circuit means.

5. An apparatus as defined in claim 4 wherein said means for supplying alternating pressure signals includes a low frequency speaker, and air channel impedance matching means for coupling said speaker to the mouth of the subject; and further comprising a direct duct means bypassing said speaker for receiving forceful exhalations from said subject while the subject is receiving alternating pressure signals.

6. An apparatus for the comprehensive measurement of pulmonary functions comprising:

means for generating alternating pressure signals, said means having a substantial output area;

means including a tapered air channel impedance matching means for coupling the substantial output area of said alternating pressure generating means to the mouth of a subject;

direct duct means bypassing said alternating pressure generating means for receiving forceful exhalations from said subject while the subject is receiving the alternating pressure signals;

means for measuring the flow of air exhaled by the subject;

means for recording the measured flow of air; and means for determining the resistance of the lungs to both steady state and alternating air flow during various portions of a breathing cycle.

7. A method of measuring pulmonary functions including the steps of:

supplying alternating pressure signals to the mouth of a subject;

measuring the flow rate of an exhalation from said subject;

measuring the resistance of the lungs to the alternating pressure applied to the mouth of the subject at a plurality of discrete expiratory volumes throughout said exhalation;

measuring the resistance of the lungs to the steady or unidirectional flow of air from the subject at a plurality of discrete expiratory volumes throughout said exhalation; and comparing the measured alternating pressure resistance with the measured resistance to steady or unidirectional flow at said plurality of discrete volumes throughout said exhalation.

8. A method as defined in claim 7 further comprising making said measurements during maximal exhalations of a subject.

9. A method as defined in claim 7 including supplying said alternating pressure signals at a frequency above six cycles per second.

10. A method as defined in claim 7 further comprising the steps of supplying gas free of nitrogen to said subject, and measuring the nitrogen content of the exhaled air.

11. A method for the comprehensive measurement of the pulmonary functions of a subject including the steps of:

supplying a measured amount of nitrogen-free gas to a subject for inhalation from a spirometer;

measuring the flow of gas inhaled by the subject;

supplying alternating pressure signals to the mouth of a subject;

measuring the flow rate of an expiration from said subject;

measuring the pressure across the lungs of the subject;

measuring the nitrogen content in exhalations from the subject;

collecting the gases exhaled by the subject;

continuously recording data from all of the measurements identified hereinabove;

determining the resistance of the lungs to the alternating pressure applied to the mouth of the subject at a plurality of different expiratory volumes throughout said expiration;

determining the resistance of the lungs to the steady or unidirectional flow or air from the subject at a plurality of different expiratory volumes throughout said exhalation; and determining the vital capacity of the lungs of the subject from the inhalation flow measurements; and determining the residual volume of the lungs from the nitrogen measurements; and recording the determined values.

12. A method for the comprehensive measurement of pulmonary functions as defined in claim 11, wherein the measurement of the pressure across the lungs of a subject includes measuring pressure utilizing an esophageal balloon, and measuring the output pressure from the mouth.

13. A method as defined in claim 11 including the step of determining differences between (1) the resistance of the lungs to the steady or unidirectional flow of air, and (2) the resistance of the lungs to the flow of air resulting from alternating pressure applied to the mouth of the subject, at a plurality of different expiratory volumes.

14. A method as defined in claim 11 including the steps of:

applying said alternating pressure signals to the mouth of a subject from a loud speaker through a tapered mechanical transition; and concurrently directing the exhaled gases through a direct path past the source of alternating pressure signals toward the location where the exhaled gases are collected.

15. A method for the comprehensive measurement of the respiratory functions of a subject including the steps of:

supplying a measured amount of nitrogen-free gas to a subject for inhalation from a spirometer;

measuring the flow of gas inhaled by the subject;

supplying alternating pressure signals to the mouth of a subject;

measuring the flow rate of an expiration from said subject;

measuring the pressure at the mouth of the subject;

measuring the nitrogen content in exhalations from the subject;

collecting the gases exhaled by the subject;

continuously recording data from all of the measurements identified hereinabove;

determining the respiratory resistance to the alternating pressure applied to the mouth of the subject at a plurality of different expiratory volumes throughout said expiration;

determining the respiratory resistance to the steady or unidirectional flow of air from the subject at a plurality of different expiratory volumes throughout said exhalation;

determining the vital capacity of the lungs of the subject from the inhalation flow measurements; and determining the residual volume of the lungs from the nitrogen measurements.

16. A method of measuring respiratory functions including the steps of:

supplying alternating pressure signals to the mouth of a subject;

measuring the flow rate of an exhalation from said subject;

measuring the resistance to the alternating pressure applied to the mouth of the subject at a plurality of discrete expiratory volumes throughout said exhalation;

measuring the resistance to the steady or unidirectional flow of air from the subject at a plurality of discrete expiratory volumes throughout said exhalation; and comparing the measured alternating pressure resistance with the measured resistance to steady or unidirectional flow at said plurality of discrete volumes throughout said exhalation.

17. An apparatus for the comprehensive measurement of pulmonary functions comprising:

a source of gas containing no nitrogen;

a closed pulmonary measurement system including an input spirometer coupled to said source of gas, for supplying a measured quantity of gas excluding nitrogen from said source to a subject;

means for collecting gas exhaled by the subject;

means including a low frequency loud speaker for supplying alternating pressure signals to the mouth of a subject;

means for measuring the flow of air inhaled by the subject;

means for measuring the flow of air exhaled by the subject;

tapered air channel impedance matching means for coupling said speaker to the mouth of the subject;

direct duct means bypassing said speaker for receiving forceful exhalation from said subject while the subject is receiving alternating pressure signals and for directing air from said forceful exhalations to said collecting means;

an esophageal balloon and transducer means having a predetermined frequency response for supplying signals to said apparatus representing the pressure across the lungs;

compensation circuit means connected to receive said signals representing the pressure across said lungs, and for correcting the frequency variations of said signals within the frequency range of interest and extending above the normal frequency of operation of said low frequency loud speaker;

means for continuously detecting the pressure at the mouth of the subject;

means for continuously monitoring the amount of nitrogen in the exhaled air;

means for recording the measured values of (1) the input flow of gas to the subject, (2) the output flow of gas from the subject, (3) the varying pressure at the mouth of the subject, (4) the compensated pressure across the lungs derived from the esophageal balloon and transducer means, and (5) the nitrogen content of the exhalations;

means for determining the resistance of the lungs to alternating pressure signals at a number of discrete points in an exhalation cycle; and means for determining the resistance of the lungs to steady gas flow at a number of discrete points in the same exhalation cycle.

* * * * *